US006730678B2

(12) United States Patent
Eickmeier et al.

(10) Patent No.: US 6,730,678 B2
(45) Date of Patent: May 4, 2004

(54) BENZOYLGUANIDINE SALT AND HYDRATES THEREOF

(75) Inventors: Christian Eickmeier, Mittelbiberach (DE); Peter Sieger, Mittelbiberach (DE); Werner Rall, Mittelbiberach (DE); Volkmar Koerner, Biberach (DE); Rolf Herter, Biberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/057,597

(22) Filed: Jan. 25, 2002

(65) Prior Publication Data

US 2002/0137753 A1 Sep. 26, 2002

Related U.S. Application Data

(60) Provisional application No. 60/281,344, filed on Apr. 4, 2001.

(30) Foreign Application Priority Data

Feb. 15, 2001 (DE) .......................................... 101 06 970

(51) Int. Cl.[7] ..................... A61K 31/496; C07D 403/06
(52) U.S. Cl. ................................. 514/254.01; 544/372
(58) Field of Search ...................... 544/372; 514/254.01

(56) References Cited

U.S. PATENT DOCUMENTS 6,114,335 A * 9/2000 Buerger et al.
6,323,207 B1 * 11/2001 Eickmeier et al.

FOREIGN PATENT DOCUMENTS

| WO | 97/262253 | * | 7/1997 |
| WO | 00/17176 | * | 3/2000 |

OTHER PUBLICATIONS

Bugge et al., Medline Abstract for Cardiovascular Research, 29(2), pp. 269–274 (1995).*
Hoque et al, Medline Abstract for Canadian Journal of Physiology and Pharmacology, 75 (4), pp. 326–334 (1997).*
Lehoux et al., Medline Abstract for Journal of Biological Chemistry, 276(19), pp. 15794–15800 (2201).*

* cited by examiner

Primary Examiner—Emily Bernhardt
(74) Attorney, Agent, or Firm—Robert P. Raymond; Timothy X. Witkowski; Anthony P. Bottino

(57) ABSTRACT

4-[4-(2-pyrrolylcarbonyl)-1-piperazinyl]-3-trifluoromethylbenzoylguanidine hydrochloride and its hydrates, processes for preparing this benzoylguanidine salt and its hydrates, pharmaceutical compositions containing this benzoylguanidine salt and its hydrates, and its use in treating diseases, particularly those in which inhibition of the cellular $Na^+/H^+$ exchange is of therapeutic benefit.

6 Claims, No Drawings

BENZOYLGUANIDINE SALT AND HYDRATES THEREOF

Related Applications

Benefit under 35 U.S.C. §119(e) of prior provisional application Ser. No. 60/281,344, filed Apr. 4, 2001, is hereby claimed.

FIELD OF THE INVENTION

The invention relates to the hydrochloride of 4-[4-(2-pyrrolylcarbonyl)-1-piperazinyl]-3-trifluoromethylbenzoylguanidine, processes for preparing it and its use in preparing a pharmaceutical composition.

BACKGROUND OF THE INVENTION

A number of benzoylguanidine derivatives are known in the art. Thus, for example, International Patent Application WO 00/17176 discloses benzoylguanidine derivatives which are characterized by valuable pharmacological properties. These compounds are effective against arrhythmias which occur in hypoxia, for example. They may also be used for complaints connected with ischaemia (such as cardiac, cerebral, gastrointestinal (such as mesenteric thrombosis/embolism), pulmonary or renal ischaemia, ischaemia of the liver, and ischaemia of the skeletal muscles). Corresponding indications include, for example, coronary heart disease, cardiac infarct, angina pectoris, stable angina pectoris, ventricular arrhythmia, subventricular arrhythmias, cardiac insufficiency, and also for assisting bypass operations, for assisting open heart surgery, for assisting operations which require an interruption to the blood supply to the heart and to assist in heart transplants, embolism in the pulmonary circulation, acute or chronic kidney failure, chronic renal insufficiency, cerebral infarct, reperfusion damage in the restoration of blood supply to areas of the brain after the break-up of vascular occlusions, and acute and chronic circulatory disorders of the brain. The abovementioned compounds may also be used in such cases in conjunction with thrombolytic agents such as t-PA, streptokinase, and urokinase.

During reperfusion of the ischemic heart (e.g., after an attack of angina pectoris or a cardiac infarct) irreversible damage may occur to cardiomyocytes in the affected region. In such cases the compounds have a cardioprotective effect, inter alia.

The category of ischaemia should also include the prevention of damage to transplants (e.g., as protection for the transplanted organ, such as, for example, liver, kidney, heart, or lung, before, during, and after implantation and during the storage of the transplant organs), which may occur in connection with transplantation. The compounds disclosed in WO 00/17176 are also pharmaceutical compositions with a protective effect in carrying out angioplastic surgical interventions on the heart and on peripheral blood vessels.

In essential hypertension and diabetic nephropathy the cellular sodium-proton exchange is increased. The compounds are therefore suitable as inhibitors of this exchange for the preventive treatment of these diseases.

The compounds are further characterized by a powerful inhibiting effect on the proliferation of cells. Therefore, the compounds are useful as medicaments in diseases where cell proliferation plays a primary or secondary part and may be used as agents against cancers, benign tumors or, for example, prostatic hypertrophy, atherosclerosis, organ hypertrophy and hyperplasia, fibrotic diseases, and late complications of diabetes.

The abovementioned pharmacologically valuable properties of the benzoylguanidine derivatives disclosed in the prior art are the main prerequisite for effective use of a compound as a pharmaceutical composition. An active substance, however, has to satisfy still more requirements in order to be allowed to be used as a medicament. These parameters are largely connected to the physico-chemical nature of the active substance.

Without being restricted thereto, examples of these parameters are the stability of effect of the starting substance under different ambient conditions, stability during the production of the pharmaceutical formulation, and stability in the finished compositions of the medicament. The pharmaceutical active substance used to prepare the pharmaceutical compositions should therefore have high stability which must also be guaranteed even under different ambient conditions. This is absolutely necessary to prevent the use of pharmaceutical compositions which contain breakdown products of the active substance, for example, in addition to the active substance itself. In such a case, the content of active substance present in pharmaceutical formulations may be lower than specified.

The absorption of moisture reduces the content of pharmaceutical active substance because of the increase in weight due to the uptake of water. Pharmaceutical compositions with a tendency to absorb moisture have to be protected from moisture during storage, for example, by the addition of suitable drying agents or by storing the pharmaceutical composition in an environment which is protected from damp. Moreover, the uptake of moisture may reduce the content of pharmaceutical active substance during manufacture if the pharmaceutical composition is exposed to the environment without any protection from moisture whatsoever. Preferably, therefore, a pharmaceutical active substance should be only slightly hygroscopic.

As the crystal modification of an active substance can influence the activity of a pharmaceutical composition, it is necessary to clarify any existing polymorphism of an active substance present in crystalline form as much as possible. If there are different polymorphic modifications of an active substance, care must be taken to ensure that the crystalline modification of the substance does not change in the subsequent pharmaceutical preparation. Otherwise, this could have a detrimental effect on the reproducible activity of the medicament. In this context, active substances which are characterized by limited polymorphism are preferred.

Another criterion which may be of exceptional importance in certain circumstances, depending on the choice of formulation or on the choice of the method of production of the formulation, is the solubility of the active substance. If, for example, pharmaceutical solutions are prepared (for example for infusions), it is essential that the active substance is sufficiently soluble in physiologically acceptable solvents. A sufficiently soluble active substance is also very important for pharmaceutical compositions administered orally.

The underlying aim of the present invention is to prepare a pharmaceutical active substance which is not only characterized by a potent pharmacological activity but also satisfies as far as possible the physico-chemical requirements referred to above.

DETAILED DESCRIPTION OF THE INVENTION

It has been found that the abovementioned aim is achieved by means of the compound 4-[4-(2- pyrrolylcarbonyl)-1-piperazinyl]-3-trifluoromethylbenzoylguanidine hydrochloride 1

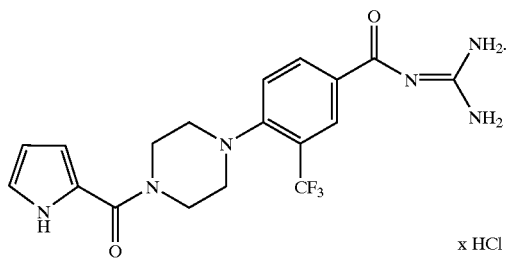

The compound of formula 1 is not hygroscopic and dissolves readily in physiologically acceptable solvents. It is also characterized by a high degree of stability.

The methanesulfonate of formula 1' disclosed in WO 00/17176

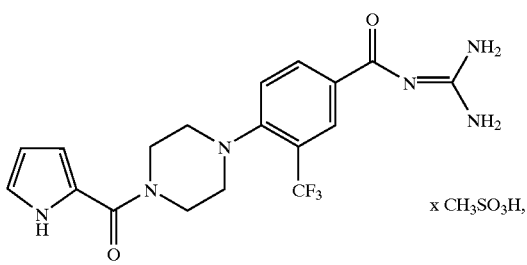

unlike the compound of formula 1, does not meet the requirements set out hereinbefore, however.

Accordingly, in one aspect, the present invention relates to the compound of formula 1 as such. In another aspect, the present invention relates to the compound of formula 1 in the form of its hydrates, preferably in the form of its monohydrate or hemihydrate.

In another aspect, the present invention relates to the use of the compound of formula 1 as a medicament. The present invention further relates to the use of the compound of formula 1, optionally in the form of its hydrates, for preparing a pharmaceutical composition for treating diseases in which inhibitors of the cellular $Na^+/H^+$ exchange may develop a therapeutic benefit.

The present invention further relates to the use of the compound of formula 1 to prepare a pharmaceutical composition for treating cardiovascular diseases.

The present invention further relates to the use of the compound of formula 1 to prepare a pharmaceutical composition for treating arrhythmia such as occurs in hypoxia, for example. The present invention further relates to the use of the compound of formula 1 to prepare a pharmaceutical composition for treating complaints connected with ischaemia (such as: cardiac, cerebral, gastrointestinal (such as mesenteric thrombosis/embolism), pulmonary, renal ischaemia, ischaemia of the liver, and ischaemia of the skeletal muscles. The present invention further relates to the use of the compound of formula 1 to prepare a pharmaceutical composition for treating diseases selected from the group consisting of coronary heart disease, cardiac infarct, angina pectoris, stable angina pectoris, ventricular arrhythmia, subventricular arrhythmias, cardiac insufficiency, and also for assisting bypass operations, for assisting open heart surgery, for assisting operations which require an interruption to the blood supply to the heart and to assist in heart transplants, embolism in the pulmonary circulation, acute or chronic kidney failure, chronic renal insufficiency, cerebral infarct, reperfusion damage in the restoration of blood supply to areas of the brain after the dissolving of vascular occlusions and acute, and chronic circulatory disorders of the brain. The present invention further relates to the use of the compound of formula 1 to prepare a pharmaceutical composition for treating diseases in which the use of cardioprotective active substances may be of therapeutic benefit. The present invention further relates to the use of the compound of formula 1 to prepare a pharmaceutical composition for treating cancers, benign tumors or, for example, prostatic hypertrophy, atherosclerosis, organ hypertrophy and hyperplasia, fibrotic diseases, and late complications of diabetes.

The compound of formula 1 may be used as an aqueous injectable solution (e.g., for intravenous, intramuscular, or subcutaneous administration), as a tablet, as a suppository, as an ointment, as a plaster for transdermal administration, as an aerosol for inhalation into the lungs or as a nasal spray.

The content of active substance in a tablet or a suppository is between 5 mg and 200 mg, preferably between 10 mg and 50 mg. For inhalation, the single dose is between 0.05 mg and 20 mg, preferably between 0.2 mg and 5 mg. For parenteral injection, the single dose is between 0.1 mg and 50 mg, preferably between 0.5 mg and 20 mg. The doses specified above may be given several times a day if necessary.

The following are some examples of pharmaceutical preparations containing the active substance:

| TABLETS | |
|---|---|
| Component | Amount (mg) |
| Compound of formula 1 | 18.0 |
| magnesium stearate | 1.2 |
| maize starch | 60.0 |
| lactose | 90.0 |
| polyvinylpyrrolidone | 1.5 |

| SOLUTION FOR INJECTION | |
|---|---|
| Component | Amount |
| Compound of formula 1 | 0.3 g |
| sodium chloride | 0.9 g |
| water for injections | ad 100 mL |

This solution can be sterilized using standard methods.

WO 00/17176 discloses possible methods of production which can be used to synthesize the free base 4-[4-(2-pyrrolylcarbonyl)-1-piperazinyl]-3-trifluoromethylbenzoylguanidine. Starting from this compound, the following possible methods of synthesizing the compound of formula 1 are illustrated by way of example.

EXAMPLE 1

4-[4-(2-pyrrolylcarbonyl)-1-piperazinyl]-3-trifluoromethylbenzoylguanidine hydrochloride 15.1 g of 4-[4-(2-pyrrolylcarbonyl)-1-piperazinyl]-3-trifluoromethylbenzoylguanidine is taken up in 151 mL of methanol and the resulting suspension is cooled to about 10° C. 16 mL of a saturated ethereal HCl solution are added to this suspension which is thus acidified to a pH of between 1 and 2. Stirring is continued, while cooling with ice, until crystallization is complete. The crystals are suction filtered, washed with cold methanol, and then with cold diethyl ether. Yield: 16.19 g; melting point: 223° C. (uncorrected).

EXAMPLE 2

4-[4-(2-pyrrolylcarbonyl)-1-piperazinyl]-3-trifluoromethylbenzoylguanidine hydrochloride hemihydrate 15.0 kg of 4-[4-(2-pyrrolylcarbonyl)-1-piperazinyl]-3-trifluoromethylbenzoylguanidine is taken and combined with 120 L of ethyl acetate. The suspension is heated to about 45° C. and combined with 30 L of water. The resulting mixture is stirred for about 15 minutes and the aqueous phase is then separated off. A solution of 3.62 kg of concentrated hydrochloric acid in 20 L of water is added to the organic phase at a constant temperature. Within about 1 to 2 hours, the mixture is cooled to 25° C. to 20° C. The hydrochloride obtained is separated off, washed with 50 L of ethyl acetate, and dried in vacuo at about 60° C. Yield: 78%; melting point: 225° C. ±5° C. (DSC at a heating rate of 10K/min).

EXAMPLE 3

4-[4-(2-pyrrolylcarbonyl)-1-piperazinyl]-3-trifluoromethylbenzoylguanidine hydrochloride monohydrate 109.4 g of 4-[4-(2-pyrrolylcarbonyl)-1-piperazinyl]-3-trifluoromethylbenzoylguanidine is suspended in 1.5 L of water and heated to about 50° C. 26.1 mL of concentrated aqueous hydrochloric acid is diluted with 300 mL of water and added dropwise to the preheated suspension within about 20 minutes. The mixture is stirred for about 15 minutes at constant temperature. Then the temperature is lowered to about 35° C. with stirring over a period of about 1.5 hours. It is then cooled to 5° C. to 10° C. and stirred for another hour at this temperature. The crystals obtained are separated off, washed with a little water, and dried in vacuo at about 50° C. Yield: 116.5 g; melting point: 180° C. ±5° C. (DSC at a heating rate of 10 K/min).

We claim:
1. A hydrate of 4-[4-(2-pyrrolylcarbonyl)-1-piperazinyl]-3-trifluoromethylbenzoylguanidine hydrochloride 1

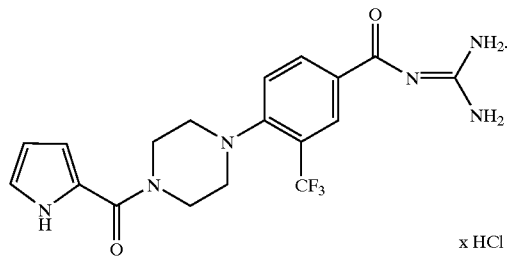

2. A monohydrate of 4-[4-(2-pyrrolylcarbonyl-1-piperazinyl]-3-trifluoromethylbenzoylguanidine hydrochloride 1

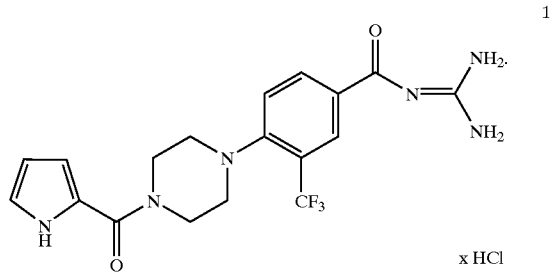

3. A hemihydrate of 4-[4-(2-pyrrolylcarbonyl)-1-piperazinyl]-3-trifluoromethylbenzoylguanidine hydrochloride 1

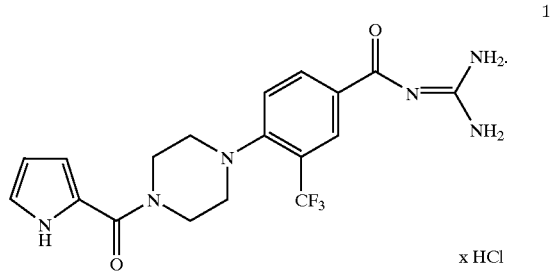

4. A pharmaceutical composition comprising:
(a) the compound according to claim 1; and
(b) a pharmaceutically acceptable excipient.
5. A pharmaceutical composition comprising:
(a) the compound according to claim 2; and
(b) a pharmaceutically acceptable excipient.
6. A pharmaceutical composition comprising:
(a) the compound according to claim 3; and
(b) a pharmaceutically acceptable excipient.

* * * * *